U
nited States Patent [19]

Clemens

[11] Patent Number: 4,992,584
[45] Date of Patent: Feb. 12, 1991

[54] PROCESS FOR THE PREPARATION OF β-KETOCARBOXIMIDES OF α,β-UNSATURATED AMIDES

[75] Inventor: Robert J. Clemens, Kingsport, Tenn.

[73] Assignee: Eastman Kodak Company, Rochester, N.Y.

[21] Appl. No.: 231,565

[22] Filed: Aug. 12, 1988

[51] Int. Cl.⁵ ............................................. C07C 231/00
[52] U.S. Cl. ................................. 564/134; 260/404.5; 556/436; 564/133; 564/155; 564/159
[58] Field of Search ............... 564/133, 159, 155, 134; 556/436; 260/404.5, 404.5 R

[56] References Cited

U.S. PATENT DOCUMENTS

| | | | |
|---|---|---|---|
| 3,228,983 | 1/1966 | John et al. | 564/159 |
| 3,912,780 | 10/1975 | Ribka et al. | 564/159 |
| 4,373,077 | 2/1983 | Boeder | 526/313 |
| 4,743,668 | 5/1988 | Fong et al. | 526/304 |

OTHER PUBLICATIONS

R. J. Clemons & J. A. Hyatt, "Acetoacetylation with 2,2,6-Trimethyl-4H-1,3-Dioxin-4-One: A Convenient Alternative to Diketene", 1985, Journal of Organic Chemistry, vol. 50, pp. 2431-2435.
Chem. Abstracts, vol. 98, Abstract No. 215599, (1983).
Masayuki Sato et al., "Synthesis of N-Acylacetoacetamide Using 2,2,6-Trimethyl-1,3-Dioxin-4-One", 1982 in Chem. Pharm. Bull., vol. 30, (No. 4), pp. 1315-1321.
Yutaka Yamamoto, "1,3-Oxazines and Related Compounds. V. N-Acylacetylation of Carboxamides with the Diketene-Halotrimethylsilane System or Acyl Meldrum's Acids", 1982 in Chem. Pharm. Bull., vol. 30, (No. 10), pp. 3505-3512.
Yutaka Yamamoto et al., "A New Method for Preparation of N-Acetoacetylcarboxamides", Synthesis, 1981, pp. 122-124.

*Primary Examiner*—Glennon H. Hollrah
*Assistant Examiner*—Scott C. Rand
*Attorney, Agent, or Firm*—J. Frederick Thomsen; William P. Heath, Jr.

[57] ABSTRACT

A process is disclosed for the preparation of β-ketocarboximides of α,β-unsaturated amides from 1,3-dioxin-4-ones and α,β-unsaturated amides using an inert solvent system capable of maintaining both reactants substantially in homogeneous solution throughout the reaction. This process provides greatly improved yields of α,β-ketocarboximides of α,β-unsaturated amides as well as a simple method of recovering same since such products can readily be precipitated from the reaction mixture.

18 Claims, No Drawings

PROCESS FOR THE PREPARATION OF β-KETOCARBOXIMIDES OF α,β-UNSATURATED AMIDES

FIELD OF INVENTION

The present invention relates to a process for the preparation of β-ketocarboximides of α,β-unsaturated amides.

BACKGROUND OF THE INVENTION

β-Ketocarboximides of α,β-unsaturated amides, such as, for example, N-acetoacetyl acrylamide, are functionalized acrylamide monomers which can be copolymerized with other acrylate or acrylamide monomers to provide crosslinkable thermoset films. It would be desirable to prepare N-acetoacetyl acrylamide directly from diketene and acrylamide. The only process known for this direct conversion involves the reaction of diketene with acrylamide in the presence of a stoichiometric amount of trimethylsilyl chloride/sodium bromide (MeCN,12h) to afford a 77% yield of N-acetoacetyl acrylamide. Unfortunately, this procedure for preparing N-acetoacetyl acrylamide directly from acrylamide and diketene is expensive and impractical for large-scale preparations. Other attempts to directly acetoacetylate acrylamide with diketene have not been successful.

An alternate process for the preparation of β-ketocarboximides from amides has been reported in the literature, involving reaction of amides with the diketene-acetone adduct, 2,2,6-trimethyl-4H-1,3-dioxin-4-one (TKD). However, low yields (<45%) are reported when this reaction of TKD with acrylamide is run neat according to this reported procedure, with even lower yields reported (~20%) when this reaction is carried out in xylene as solvent.

There is, therefore, a need for an improved process for synthesizing β-ketocarboximides of α,β-unsaturated amides wherein the desired acrylamide is obtained in high yield and product recovery is readily accomplished.

OBJECTS OF THE INVENTION

Accordingly, it is an object of the present invention to provide a process for the preparation of β-ketocarboximides of α,β-unsaturated amides in high yield.

It is a further object of the present invention to provide a solvent system useful in the preparation of β-ketocarboximides of α,β-unsaturated amides which generates a homogeneous reaction solution.

These and other objects of the present invention will be apparent to those of skill in the art from the disclosure and claims which follow.

STATEMENT OF THE INVENTION

In accordance with the present invention, I have discovered that β-ketocarboximides of α,β-unsaturated amides can be prepared in high yield by reaction of an α,β-unsaturated amide and a 1,3-dioxin-4-one when the reaction is carried out in the presence of a polymerization inhibitor and an inert solvent system which maintains both the reactants and reaction product in solution.

DETAILED DESCRIPTION OF THE INVENTION

The present invention provides a process for the preparation of β-ketocarboximides of α,β-unsaturated amides which process comprises heating a homogeneous reaction mixture comprising an α,β-unsaturated amide, a 1,3-dioxin-4-one, and a polymerization inhibitor in an inert solvent system which is capable of maintaining the α,β-unsaturated amide and the 1,3-dioxin-4-one solution. The present invention also contemplates the further steps of removing the carbonyl-containing reaction by-product from the reaction mixture during the reaction and recovering the β-ketocarboximides of α,β-unsaturated amides from the reaction mixture.

The process of the present invention provides a commercially desirable method of preparing β-ketocarboximides of α,β-unsaturated amides of the following structure:

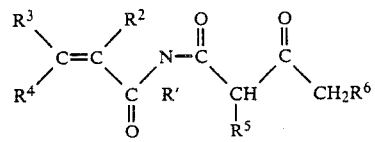

wherein $R'$ is H or $C_1-C_{10}$ alkyl or aromatic or substituted alkyl or aromatic moiety; each of $R^2$, $R^3$ and $R^4$ are independently H or $C_1-C_{10}$ alkyl, and each of $R^5$ and $R^6$ are independently selected from $C_1-C_{10}$ alkyl, aryl, alkaryl, aralkyl or trialkylsilane moieties, and $R^6$ may additionally be hydrogen. The invention process involves the reaction of a 1,3-dioxin-4-one having the structure:

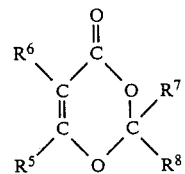

wherein each of $R^7$ and $R^8$ are independently H or $C_1$ up to $C_6$ alkyl or aryl, with the proviso that the total number of carbon atoms for $R^7+R^8$ is no greater than 8; wherein each of $R^5$ and $R^6$ are independently selected from $C_1-C_{10}$ alkyl, aryl, alkaryl, aralkyl or trialkylsilane moieties and $R^6$ may additionally be hydrogen, with an α,β-unsaturated amide having the structure:

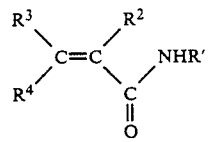

wherein $R^1$ is H or $C_1-C_{10}$ alkyl or aromatic substituted alkyl, and each of $R^2$, $R^3$ and $R^4$ are independently H or $C_1-C_{10}$ alkyl to form β-ketocarboximides of α,β-unsaturated amides.

The invention process is carried out in an inert solvent system capable of maintaining the α,β-unsaturated amide and 1,3-dioxin-4-one in homogeneous solution, and produces a considerably higher yield of β-ketocarboximides of α,β-unsaturated amides than is obtained with prior art processes. The use of an inert solvent is an improvement because it dissolves both the 1,3-dioxin-4-one and the α,β-unsaturated amide to form a homogeneous reation mixture and because the inert solvent is not consumed by the acetoacetylation reaction. Thus, as a result, the reaction mixture remains substantially homogeneous throughout the reaction. As a result, loss of starting materials and/or product by polymerization and/or runaway reactions are avoided because locally high concentrations of reactants or products are avoided in the practice of the invention.

The inert solvent system employed in the practice of the present invention comprises any solvent which is capable of maintaining the combination of $\alpha,\beta$-unsaturated amide, 1,3-dioxin-4-one and the non-nucleophilic free radical inhibitor in substantially homogeneous solution. Preferred inert solvent systems comprise non-nucleophilic, oxygenated solvents having in the range of 2 up to 12 carbon atoms, which solvents have a boiling point in the range of about 75° up to 250° C., since the reaction rate between the $\alpha,\beta$-unsaturated amide and the 1,3-dioxin-4-one becomes undesirably slow below this temperature. Another factor to be considered when choosing the solvent system is the ease with which the carbonyl-containing reaction by-product can be removed therefrom.

The polarity of the solvent system is a good indicator of how effective it will be for use in the practice of the present reaction. Thus, while the solvent system must be polar enough to dissolve the reactants, less polar solvent systems tend to reduce the undesirable polymerization reaction of both the $\alpha,\beta$-unsaturated amide and $\beta$-ketocarboximides of $\alpha,\beta$-unsaturated amides as well as facilitate the recovery of $\beta$-ketocarboximides of $\alpha,\beta$-unsaturated amides from the reaction mixture.

The inert solvent system employed in the practice of the present invention can also be a combination of several inert materials so long as the resulting combination has the desirable properties. For example, the inert solvent system can be a mixture of a non-nucleophilic, oxygenated solvent and a non-polar hydrocarbon solvent. The proportions of this mixture can be adjusted to provide a solvent system having the appropriate boiling point and polarity; with the proviso that enough of the inert solvent system will desirably be present to maintain both the $\alpha,\beta$-unsaturated amide and the 1,3-dioxin-4-one substantially in homogeneous solution.

Exemplary non-nucleophilic, oxygenated solvents include ethers such as glyme and diglyme, amides such as dimethylformamide, dimethylacetamide, N-methylpyrrolidinone, sulfoxides such as dimethylsulfoxide, carboxylic acid esters having in the range of 4 up to 12 carbon atoms, mixed ether-ester moieties, and the like, as well as mixtures of any two or more thereof.

The preferred non-nucleophilic, oxygenated solvents employed in the practice of the present invention are alkyl esters having in the range of about 4 up to 10 carbon atoms, for example, ethyl acetate, n-propyl acetate and n-butyl acetate. The most preferred non-nucleophilic, oxygenated solvent for use in the practice of the present invention is n-butyl acetate due to its ability to maintain the combination of $\alpha,\beta$-unsaturated amide, 1,3-dioxin-4-one and the non-nucleophilic free radical inhibitor in substantially homogeneous solution. n-Butyl acetate is especially preferred because it has a boiling point near 120° C. which is the lowest temperature that provides a reasonable rate of reaction between the $\alpha,\beta$-unsaturated amide and the 1,3-dioxin-4-one.

Exemplary non-polar hydrocarbons which can optionally be employed in combination with the non-nucleophilic, oxygenated solvent include: aromatic hydrocarbons having in the range of 6 up to 10 carbon atoms, e.g., benzene; aliphatic hydrocarbons having in the range of 5 up to 8 carbon atoms, e.g., hexane or heptane; alkaryl or aralkyl hydrocarbons having in the range of 7 up to 12 carbon atoms, e.g., toluene or xylene; cycloaliphatic hydrocarbons having in the range of 5 up to 10 carbon atoms; and the like, as well as mixtures of any two or more thereof.

Preferred non-polar hydrocarbons employed in the practice of the present invention include xylene and toluene.

In the presently most preferred embodiment of the present invention, a mixture of non-nucleophilic, oxygenated solvent and non-polar hydrocarbon solvent is employed; where the ratio of non-polar hydrocarbon to oxygenated solvent is maintained as high as possible while still maintaining a substantially homogeneous reaction mixture under the reaction conditions. Suitable ratios of non-polar hydrocarbon to oxygenated solvent will vary as a function of the degree of conversion of the $\alpha,\beta$-unsaturated amide. Ratios up to about 10:1 are suitable. Typically, lower ratios are appropriate at low degrees of conversion (i.e., higher concentrations of unreacted amide), while higher ratios are useful at higher degrees of conversion (i.e., lower concentrations of unreacted amide).

It has been found that the resulting solvent system produces higher yields of $\beta$-ketocarboximides of $\alpha,\beta$-unsaturated amides. In addition, the carbonyl-containing reaction by-product and inert solvent system which distill out of the reaction vessel during the reaction can be replaced by a solvent mixture enriched in the non-polar hydrocarbon relative to the ratio of components in the initial solvent. For example, where the initial mixture employed contains about 50% oxygenated solvent (e.g., n-butyl acetate) and 50% non-polar hydrocarbon (e.g., xylene), the solvent removed by distillation during the reaction can be replaced by a mixture of about 33% oxygenated solvent and 67% xylene. This replacement of some of the oxygenated solvent with non-polar hydrocarbon results in an even less polar reaction mixture. The reduction in the polarity of the reaction mixture virtually eliminates the formation of polymeric by-products, and facilitates the recovery of the highly soluble $\beta$-ketocarboximides of $\alpha\beta$-unsaturated amides from the less polar reaction medium. This replacement is possible since the consumption of some of the initial reactants means that less oxygenated solvent is now needed to maintain the $\alpha,\beta$-unsaturated amide and the 1,3-dioxin-4-one in solution. Experimental results have demonstrated yields as high as 77% for this process.

The process of the present invention is carried out in the presence of a small amount of a non-nucleophilic free radical polymerization inhibitor to prevent undesirable polymerization of the $\alpha,\beta$-unsaturated amide during the reaction. Suitable polymerization inhibitors include diphenylnitrosamine, butylated hydroxytoluene (BHT), benzoquinone (BQ), and the like. Enough polymerization inhibitor is added to effectively reduce the undesirable polymerization of the $\alpha,\beta$-unsaturated amide under the reaction conditions.

The process of the invention is carried out by heating a combination of an $\alpha,\beta$-unsaturated amide, a 1,3-dioxin-4-one and a non-nucleophilic free radical inhibitor in an inert solvent system. The combination of an $\alpha,\beta$-unsaturated amide, a 1,3-dioxin-4-one and a non-nucleophilic free radical inhibitor can be brought together in any sequence. For example, the amide component can be dissolved in the solvent system first, then the 1,3- dioxin-4-one can be added, or vice versa. The polymerization inhibitor can be added to the reaction mixture at any convenient point during the combining process, so long as it is present in the reaction system when the α,β-unsaturated amide is subjected to elevated temperatures.

The reaction between the α,β-unsaturated amide and the 1,3-dioxin-4-one will form β-ketocarboximides of α,β-unsaturated amides and a carbonyl-containing by-product. The production of high yields of the desired reaction product is aided by removal of the carbonyl-containing by-product from the reaction mixture during the course of the reaction. The carbonyl-containing by-product can be replaced by additional quantities of inert solvent, especially non-polar hydrocarbon.

Once the reaction is complete, the β-ketocarboximides of α,β-unsaturated amides can be readily recovered by known methods. The preferred method of recovery is precipitation from the reaction mixture by cooling the solution upon completion of the reaction, or, alternatively adding sufficient additional quantities of the non-polar hydrocarbons so as to cause precipitation of the desired product.

The β-ketocarboximides of α,β-unsaturated amides, e.g., N-acetoacetyl acrylamide, generated by the process of the present invention, is an off-white, crystalline solid which typically polymerizes at its melting point (129°–130° C.). It is slightly soluble in water and is freely soluble in many organic solvents. N-acetoacetyl acrylamide is amenable to copolymerization in either aqueous or organic systems, and is useful in coatings and films just as are other unsaturated amides.

In order to further illustrate the process of the present invention, the following examples are included. It will be understood that the examples are provided for illustrative purposes only and are not to be restrictive of the scope of the invention as herein described and set forth in the claims.

EXAMPLE 1

Acrylamide (284 g, 2 mol) and N,N-diphenylnitrosamine (0.4 g, 2 mmol) were dissolved in a mixture of 150 mL of n-butyl acetate and the resulting solution was heated at a rapid rate. When the solution temperature reached 80° C., 2,2,6-trimethyl-4H-1,3-dioxin-4-one (TKD, 268 g, 2 mol) was added at a rate of 40 mL min$^{-1}$ while the external heating continued; 220 mL of liquids was removed via a distillation takeoff before the reaction temperature of 124° C. (b.p. of nBuOAc) was reached. Thirty minutes after the start of the TKD addition, the reaction was filtered while hot, and poured into 600 mL of hexanes. The precipitated product was collected, air dried, and washed with cold water to remove any residual acrylamide. Yields of the resulting off-white solid mp 127°–130° C., varied from 69%–77% over several trials.

EXAMPLE 2

A solution of acrylamide (71 g, 1 mol), 2,2,6-trimethyl-4H-1,3-dioxin-4-one (TKD) (146 g, 1 mol at 98% assay), and N,N-diphenylnitrosamine (0.2 g, 1 mmol) in a mixture of 50 mL of n-butyl acetate and 50 mL of xylenes was heated to 125° C. in a 500 mL three-neck flask equipped with a thermometer, an addition funnel, and a distillation takeoff. As the reaction temperature exceeded 115° C., acetone began to be liberated, and a total of 90 mL of distillate was removed as the temperature reached 123° C. This distillate was replaced via a dropwise addition of a solution of 50 mL of xylene and 25 mL of n-butyl acetate, so that the reaction volume remained constant. The reaction was maintained at reflux (125° C.) for 20 minutes. The resulting orange solution was filtered while hot to remove any polymeric impurities, and the product allowed to crystallize by cooling. The crystals were collected by filtration, washed with a small quantity of hexane, and dried to afford 119 g (77%) of off-white-tan crystals, mp 128°–130° C. Gas chromatographic analysis indicated that additional product remained in the filtrate. The product could be decolorized via recrystallization from a mixture of ethyl acetate/hexane, to afford colorless crystals of the same melting point.

IR (KBr) 3425, 3300, 2960, 1750, 1710(s), 1690(s), 1620, 1490, 1150 cm$^{-1}$;

NMR (CDCl$_3$) 75/25 keto/enol mixture 9.0 (keto) and 8.2 (enol) (br s, NH), 6.48 (d, J=17 Hz, 1H) 6.33 (complex d of d, J=11, 17 Hz 1H), 5.91 (d, J=11 Hz 1H), 3.93 (s, 2H, keto, CH$_2$), 2.32 (keto) and 2.07 (enol) (s, 3H, CH$_3$). The spectrum shifts significantly in d$_6$-DMSO.

Calculated Analysis for C$_7$H$_9$NO$_3$: C, 54.2; H, 5.85; N, 9.03.

Actual Analysis Found: C, 53.8; H, 5.74; N, 8.94.

EXAMPLE 3

A solution of acrylamide (21.3 g, 0.3 mol), butylated hydroxytoluene (BHT, 0.66 g, 1%) and benzoquinone (BQ, 0.22 g, 0.7%) in a mixture of 75 mL of xylene and 150 mL of n-butyl acetate was heated to about 80° C. When the reaction mixture reached 80° C., 42.6 g (0.3 mol) of 2,2,6-trimethyl-4H-1,3-dioxin-4-one was added as a small stream over a period of about 10 minutes; the reaction mixture was then heated rapidly up to about 120° C., and maintained at that temperature for about 10 minutes. Once heating of the reaction mixture was complete, the reaction mixture was allowed to cool and 29.4 g (63% yield; mp 128° to 130° C.) of N-acetoacetyl acrylamide was collected as a white precipitate and air dried.

The invention has been described in detail with particular reference to preferred embodiments thereof, but it will be understood that variations and modification can be effected within the spirit and scope of the invention.

That which is claimed is:

1. A process for the preparation of β-ketocarboximides of acrylamide, said process comprising:
   heating a combination comprising:
   (i) acrylamide;
   (ii) a 1,3-dioxin-4-one;
   (iii) a non-nucleophilic free radical inhibitor; and
   (iv) an inert solvent system comprising an alkyl ester having 4 to 10 carbon atoms.

2. A process according to claim 1 wherein said solvent comprises n-butyl acetate.

3. A process according to claim 1 wherein said inert solvent system further comprises a nonpolar hydrocarbon solvent.

4. A process according to claim 3 wherein said hydrocarbon solvent is selected from the group consisting of:
   aromatic hydrocarbons having in the range of 6 up to 10 carbon atoms,
   aliphatic hydrocarbons having in the range of 5 up to 8 carbon atoms, alkaryl or aralkyl hydrocarbon having in the range of 7 up to 12 carbon atoms, cycloaliphatic hydrocarbons having in the range of 5 up to 10 carbon atoms, as well as mixtures of any two or more thereof.

5. A process according to claim 4 wherein said non-polar hydrocarbon solvent is xylene.

6. A process according to claim 3 wherein the ratio of non-polar hydrocarbon solvent to oxygenated solvent is maintained at as high a ratio as possible while still producing a homogeneous reaction mixture under reaction conditions.

7. A process according to claim 6 wherein the ratio of non-polar hydrocarbon solvent to oxygenated solvent is maintained at a value up to about 10:1.

8. A process according to claim 7 wherein said ratio varies as a function of the degree of conversion of the acrylamide.

9. A process according to claim 1 wherein said 1,3-dioxin-4-one has the structure:

$$\begin{array}{c} R^6 \\ \diagdown \\ C \\ \diagup \\ R^5 \end{array} \begin{array}{c} O \\ \| \\ C \\ \| \\ C \end{array} \begin{array}{c} \diagup \\ O \\ \diagdown \\ C \\ \diagdown \end{array} \begin{array}{c} R^7 \\ \diagup \\ R^8 \end{array}$$

wherein each of $R^7$ and $R^8$ are independently H or $C_1$ up to $C_6$ alkyl or aryl, with the proviso that the total number of carbon atoms for $R^7 + R^8$ is no greater than 8; and wherein each of $R^5$ and $R^6$ are independently selected from the group consisting of $C_1$-$C_{10}$ alkyl, aryl, alkaryl, aralkyl and trialkylsilane groups, and $R^6$ may additionally be hydrogen.

10. A process according to claim 9 wherein the total number of carbon atoms for $R^7 + R^8$ of said 1,3-dioxin-4-one falls within the range of 1 up to 8, and wherein $R^5$ = methyl and $R^6$ = hydrogen.

11. A process according to claim 10 wherein said 1,3-dioxin-4-one is 2,2,6-trimethyl-4H-1,3-dioxin-4-one.

12. A process according to claim 1 wherein said 1,3-dioxin-4-one is employed in substantially stoichiometric proportion with the acrylamide.

13. A process according to claim 1 wherein a sufficient quantity of said inhibitor is employed to substantially inhibit polymerization of the acrylamide.

14. A process according to claim 13 wherein said inhibitor is selected from the group consisting of:
butylated hydroxytoluene (BHT),
benzoquinone (BQ),
N,N-diphenylnitrosamine,
as well as mixtures of any two or more thereof.

15. A process according to claim 1 which further comprises removing carbonyl-containing reaction by-product from said solution during said reaction.

16. A process according to claim 15 further comprising adding to said reaction mixture an additional quantity of said solvent system, said additional quantity being equal to at least a portion of the volume of carbonyl-containing reaction by-product removed from said reaction mixture.

17. A process according to claim 16 wherein the amount and timing of said addition are such as to maintain the volume of said reaction mixture substantially constant.

18. A process according to claim 3 wherein additional non-polar hydrocarbon solvent is added to the reaction mixture once said heating of (i), (ii), (iii) and (iv) is complete so as to cause precipitation of the reaction product.

* * * * *